(12) United States Patent
Elliott et al.

(10) Patent No.: US 7,351,192 B2
(45) Date of Patent: Apr. 1, 2008

(54) SELECTIVELY LOADABLE/SEALABLE BIORESORBABLE CARRIER ASSEMBLY FOR RADIOISOTOPE SEEDS

(75) Inventors: Daniel M. Elliott, Shorewood, MN (US); George M. Hoedeman, Eden Prairie, MN (US); John J. Berkey, St. Louis Park, MN (US)

(73) Assignee: Core Oncology, Inc., Tampa, FL (US)

( * ) Notice: Subject to any disclaimer, the term of this patent is extended or adjusted under 35 U.S.C. 154(b) by 622 days.

(21) Appl. No.: 10/853,575

(22) Filed: May 25, 2004

(65) Prior Publication Data
US 2007/0135673 A1    Jun. 14, 2007

(51) Int. Cl.
*A61N 5/00* (2006.01)
(52) U.S. Cl. .......................................................... 600/1
(58) Field of Classification Search ................ 600/1–8, 600/300; 128/897, 898
See application file for complete search history.

(56) References Cited

U.S. PATENT DOCUMENTS

| | | | |
|---|---|---|---|
| 4,167,179 A | 9/1979 | Kirsch | |
| 4,323,055 A | 4/1982 | Kubiatowiez | |
| 4,509,506 A | 4/1985 | Windorski et al. | |
| 4,697,575 A | 10/1987 | Horowitz | |
| 4,815,449 A | 3/1989 | Horowitz | |
| 5,242,373 A | 9/1993 | Scott et al. | |
| 5,460,592 A | 10/1995 | Langton et al. | |
| 5,713,828 A | 2/1998 | Coniglione | |
| 5,851,173 A | 12/1998 | Dugan | |
| 5,860,909 A | 1/1999 | Mick et al. | |
| 5,906,574 A * | 5/1999 | Kan | 600/7 |
| 5,928,130 A | 7/1999 | Schmidt | |
| 5,938,583 A | 8/1999 | Grimm | |
| 6,010,446 A | 1/2000 | Grimm | |
| 6,080,099 A | 6/2000 | Slater et al. | |
| 6,113,529 A * | 9/2000 | Shi | 600/7 |
| 6,159,143 A | 12/2000 | Lennox | |
| 6,163,947 A | 12/2000 | Coniglione | |
| 6,221,003 B1 | 4/2001 | Sierocuk et al. | |
| 6,264,599 B1 | 7/2001 | Slater et al. | |
| 6,264,600 B1 | 7/2001 | Grimm | |
| 6,273,851 B1 | 8/2001 | Slater et al. | |
| 6,347,443 B2 | 2/2002 | Coniglione | |
| 6,358,195 B1 | 3/2002 | Green et al. | |
| 6,402,677 B1 | 6/2002 | Jacobs | |
| 6,450,937 B1 | 9/2002 | Mercereau et al. | |
| 6,450,938 B1 | 9/2002 | Miller | |
| 6,530,875 B1 | 3/2003 | Taylor et al. | |

(Continued)

OTHER PUBLICATIONS

Amersham Health, Rapid Strand, *Instructions for the use of RAPID Strand for Interstitial Brachytherapy Treatments*, May 2003, pp. 1-12.

Primary Examiner—Samuel G. Gilbert
(74) Attorney, Agent, or Firm—DLA Piper US LLP

(57) ABSTRACT

A selectively loadable/sealable bioresorbable carrier assembly for retaining and positioning elements used in brachytherapy procedures comprises a bioresorbable tube having a closed distal end and a proximal open end. The bioresorbable tube is loaded with a selectable arrangement of elements, including at least one radioactive seed, through the proximal open end. After the bioresorbable tube is selectably loaded, the bioresorbable tube is heat sealed at a sealing position adjacent a proximalmost element. Once sealed, the bioresorbable tube maintains the arrangement of elements throughout the treatment duration.

22 Claims, 13 Drawing Sheets

U.S. PATENT DOCUMENTS

| | | |
|---|---|---|
| 6,537,192 B1 | 3/2003 | Elliott et al. |
| 6,554,760 B2 | 4/2003 | Lamoureux et al. |
| 6,558,309 B2 | 5/2003 | Hogendijk et al. |
| 6,572,527 B2 | 6/2003 | Steele, Sr. et al. |
| 6,585,633 B2 | 7/2003 | Vitali et al. |
| 6,599,231 B1 | 7/2003 | Hoedeman et al. |
| 6,599,233 B1 | 7/2003 | Bede et al. |
| 6,616,593 B1 | 9/2003 | Elliott et al. |
| 6,635,008 B1 | 10/2003 | Liprie |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,622 B2 | 12/2003 | Reed et al. |
| 6,679,824 B1 | 1/2004 | Reed et al. |
| 6,682,471 B2 | 1/2004 | Steele, Sr. et al. |
| 6,709,381 B2 | 3/2004 | Munro, III |
| 6,761,680 B2 | 7/2004 | Terwilliger et al. |
| 6,869,390 B2 | 3/2005 | Elliott et al. |
| 2002/0013509 A1 | 1/2002 | Schmidt |
| 2002/0120174 A1 | 8/2002 | Steele, Sr. et al. |
| 2002/0177748 A1 | 11/2002 | Munro, III |
| 2003/0018232 A1 | 1/2003 | Elliott et al. |
| 2003/0028068 A1 | 2/2003 | Steele, Sr. et al. |
| 2003/0045769 A1 | 3/2003 | Kalas et al. |
| 2003/0109769 A1 | 6/2003 | Lowery et al. |
| 2003/0139641 A1 | 7/2003 | Hoedeman et al. |
| 2003/0139700 A1 | 7/2003 | Elliott et al. |
| 2003/0149328 A1 | 8/2003 | Elliott et al. |
| 2003/0171639 A1 | 9/2003 | Taylor et al. |
| 2003/0176759 A1 | 9/2003 | Hogendijk et al. |
| 2003/0191355 A1 | 10/2003 | Ferguson |
| 2003/0220535 A1 | 11/2003 | Ferguson |
| 2003/0225437 A1 | 12/2003 | Ferguson |
| 2004/0225176 A1 | 11/2004 | Flanagan et al. |

* cited by examiner

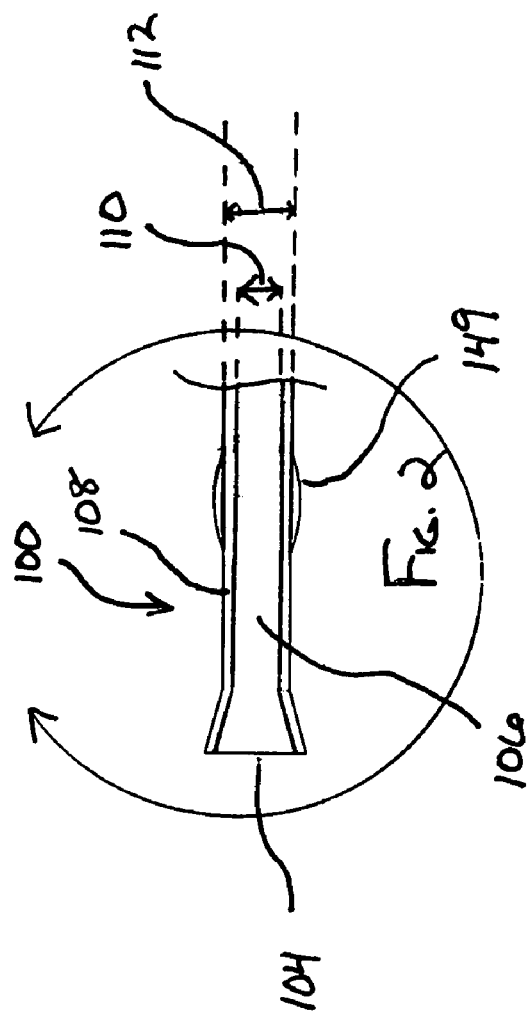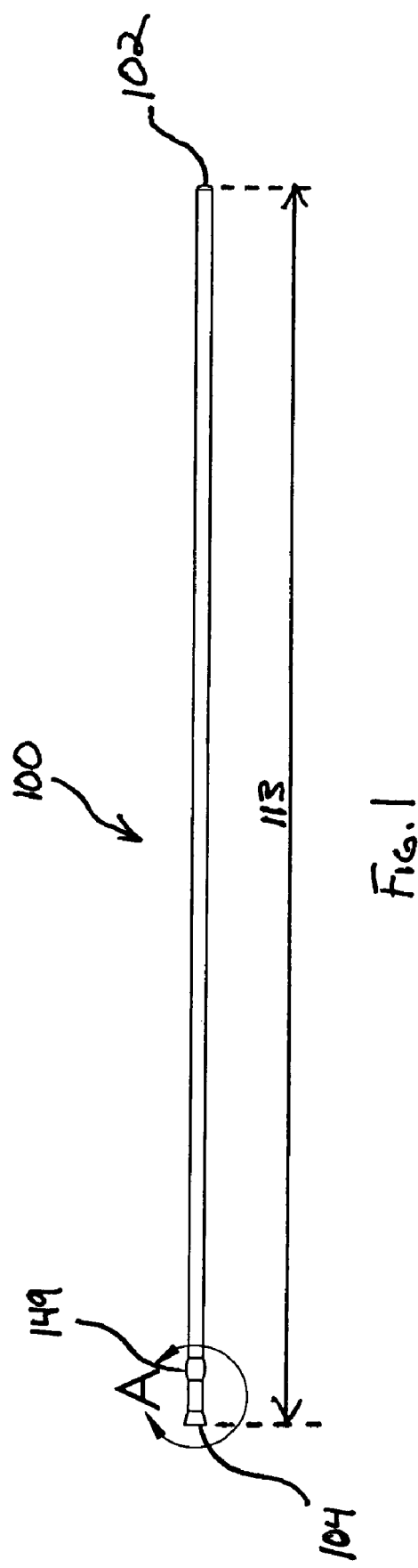

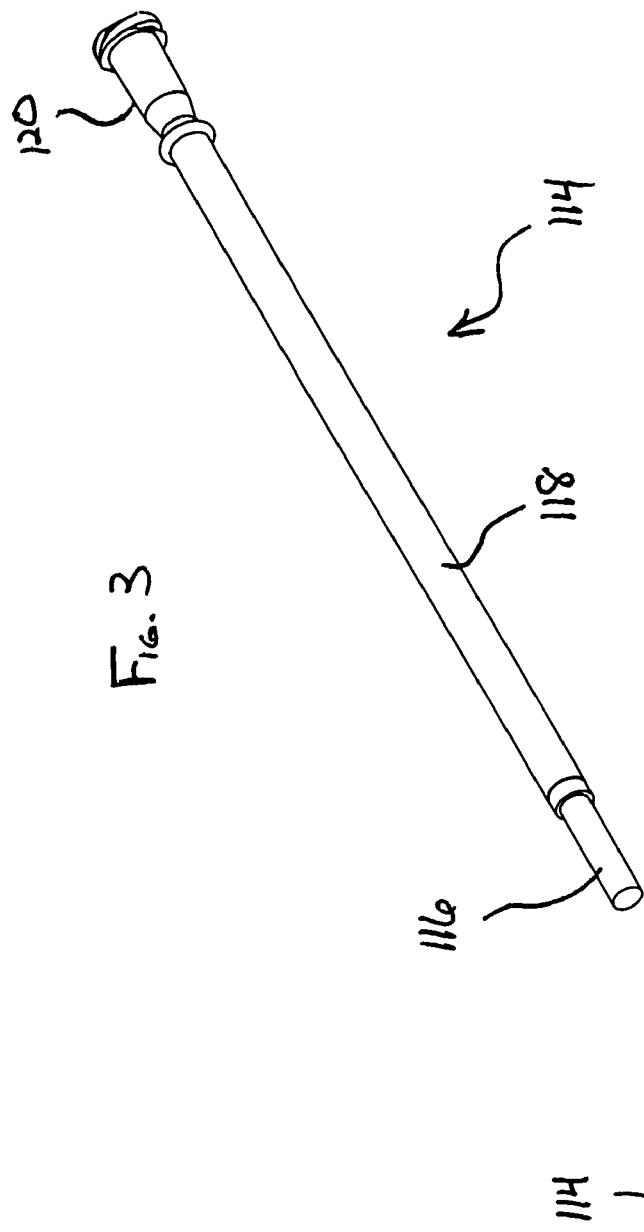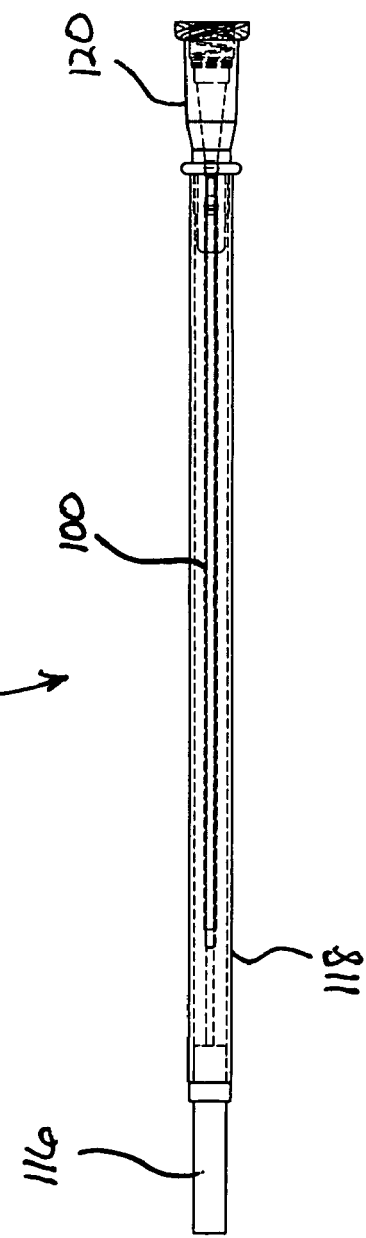

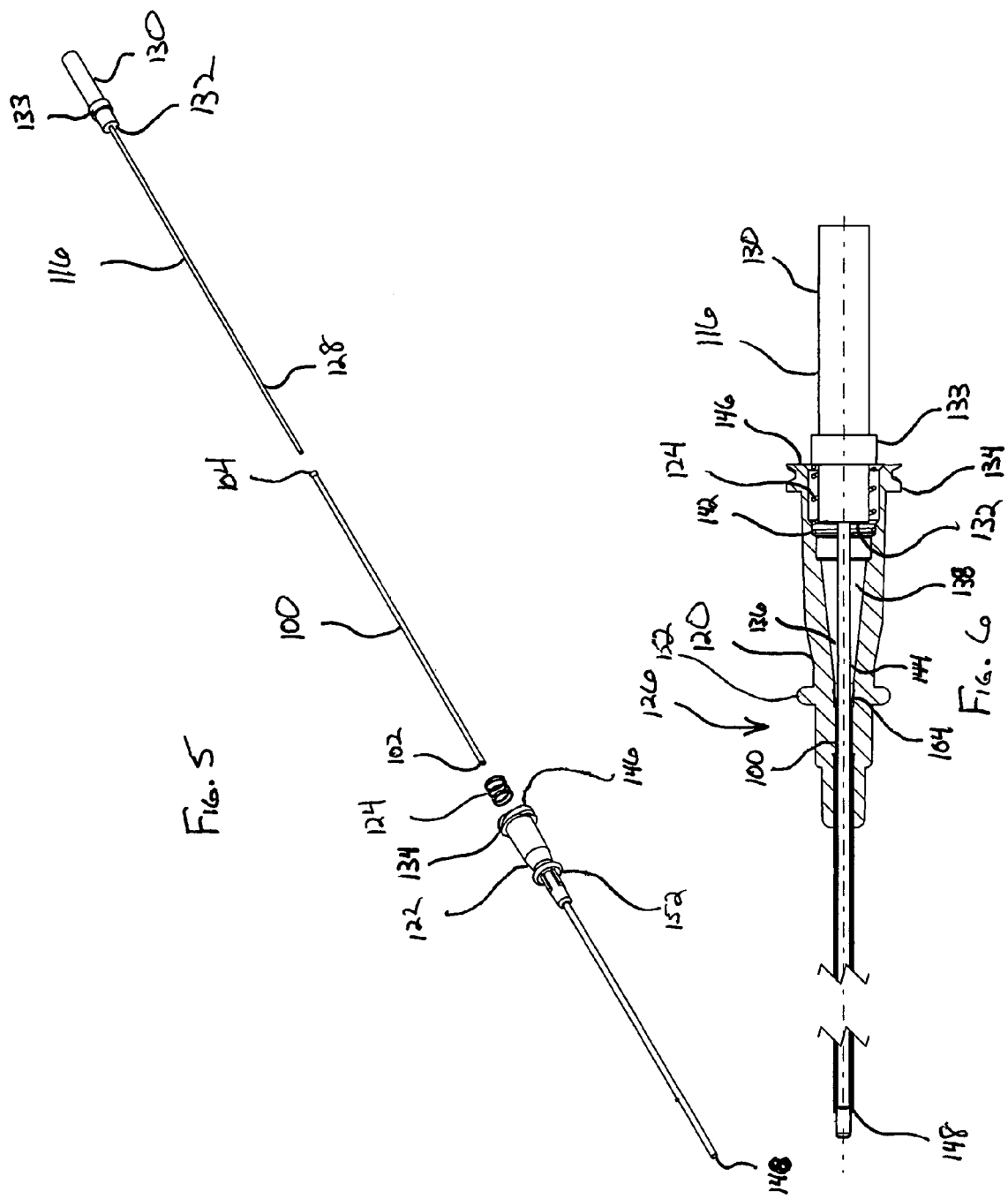

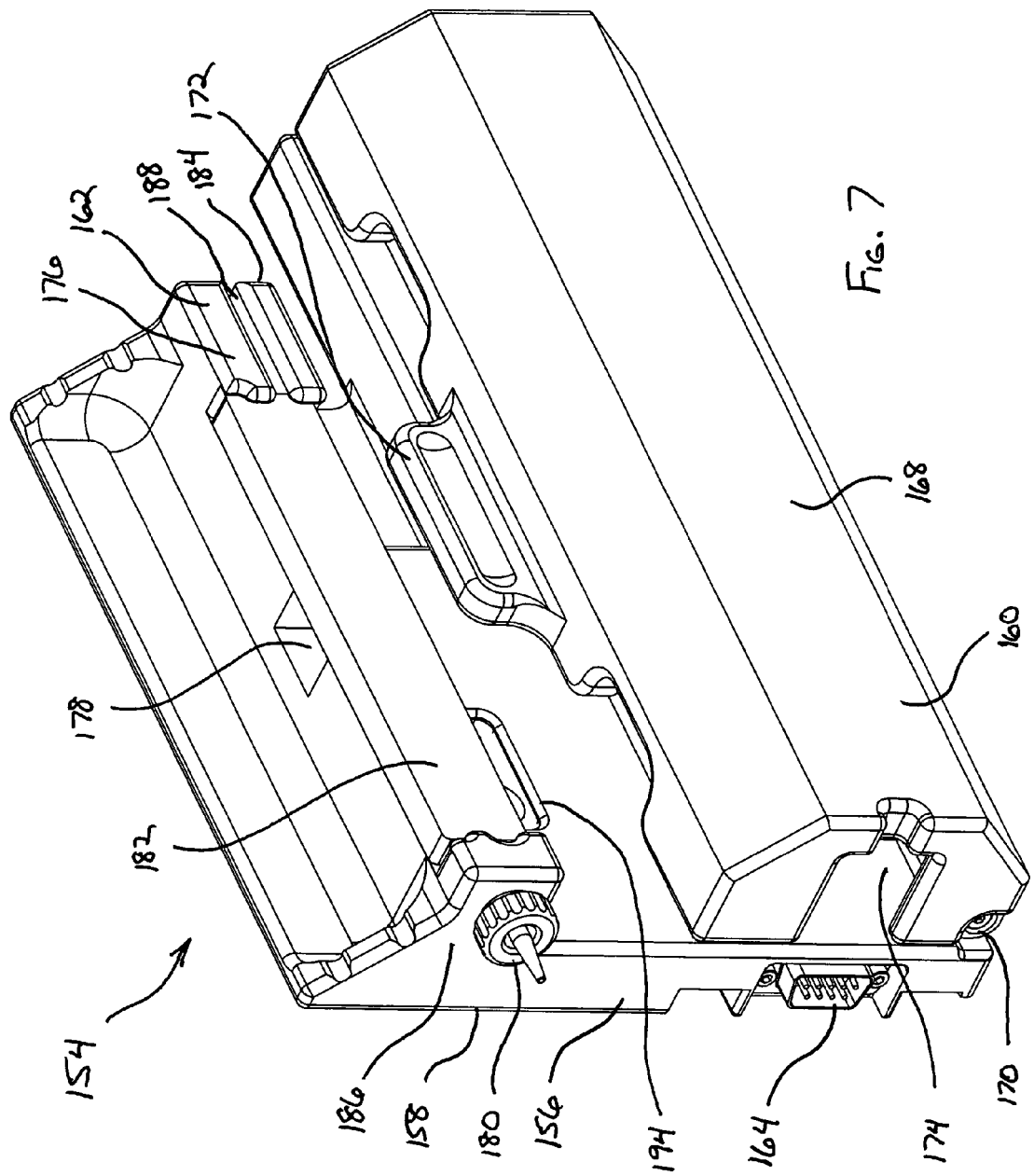

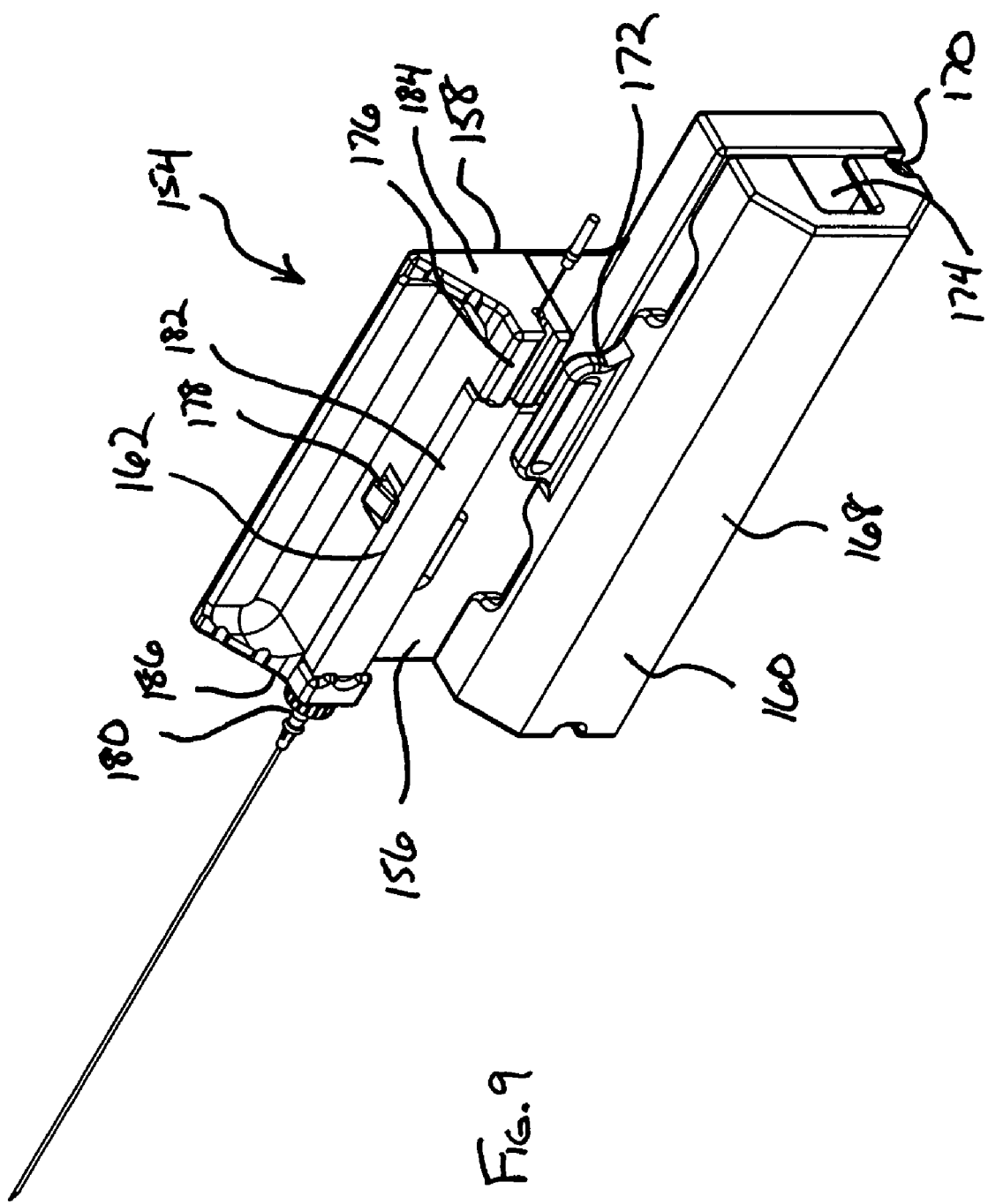

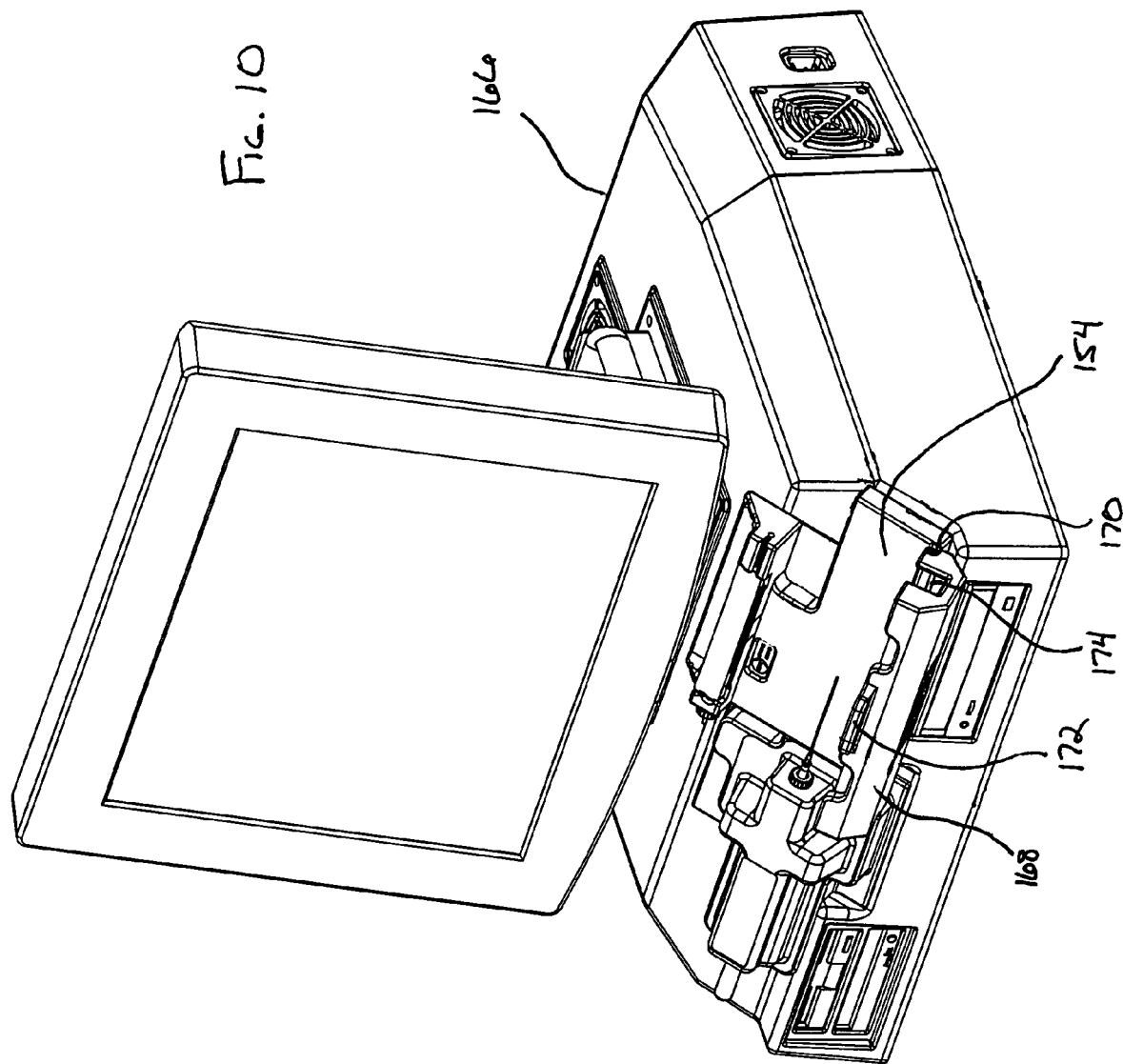

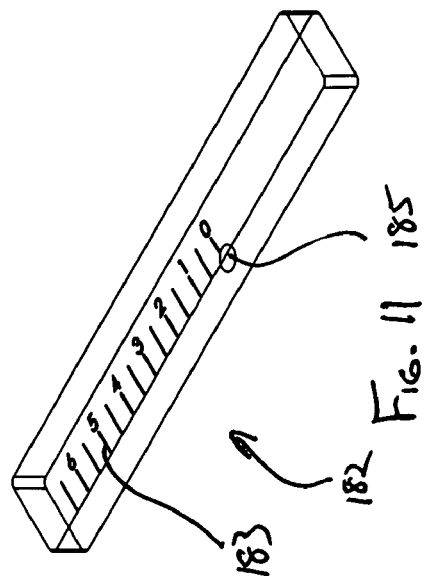
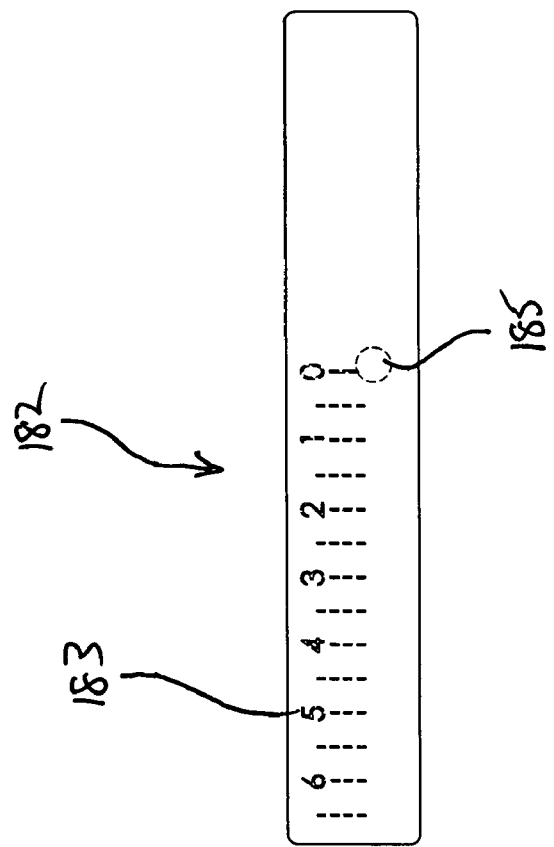

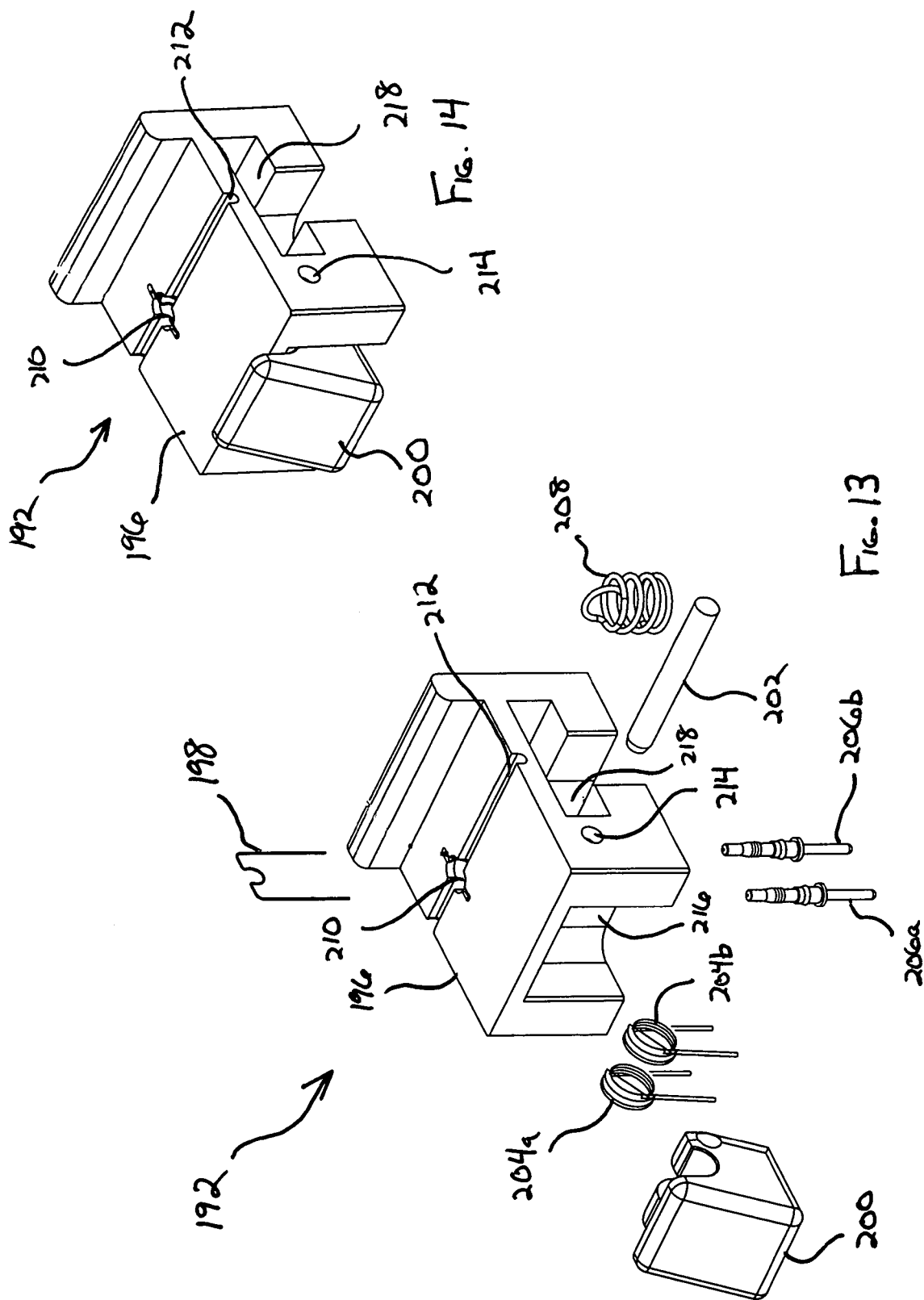

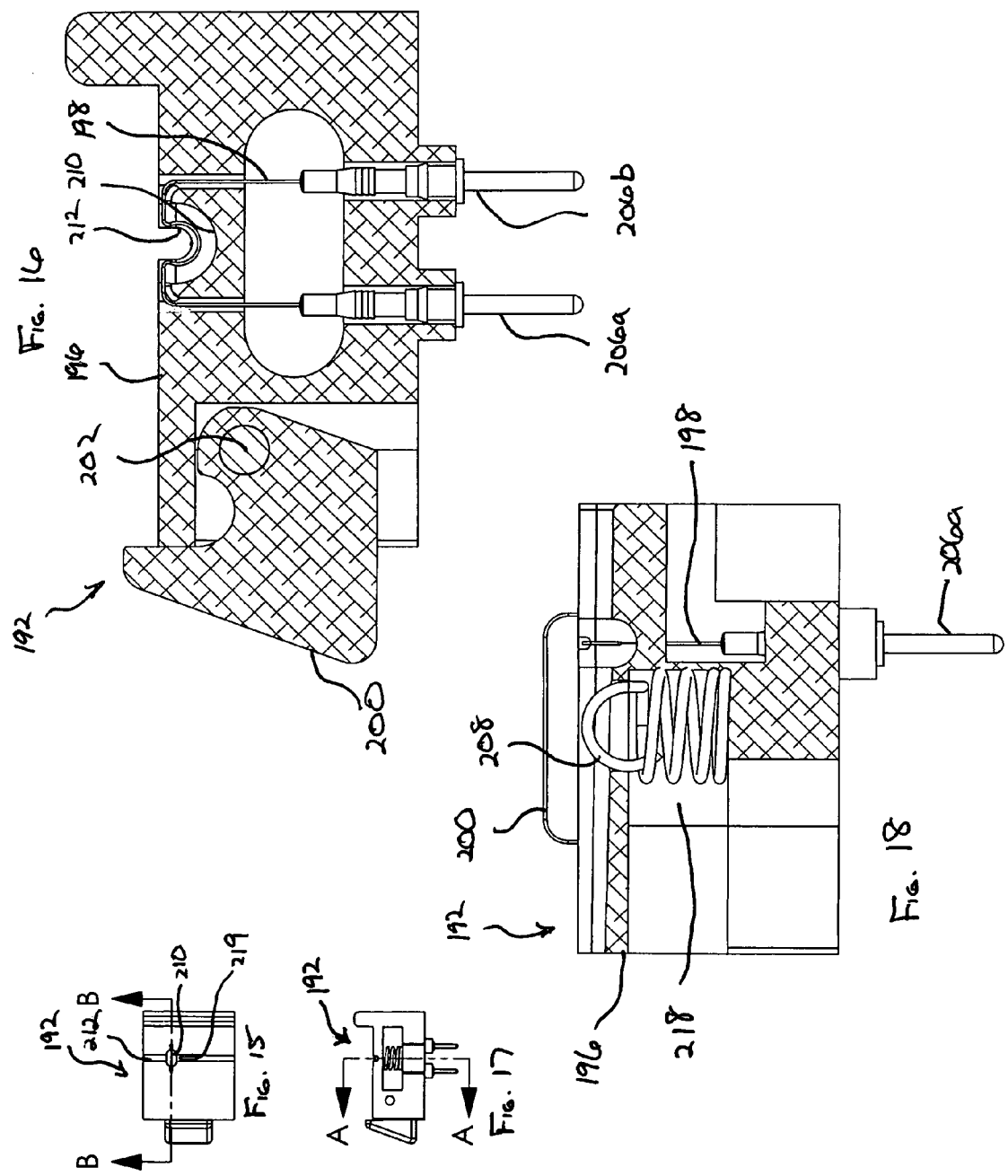

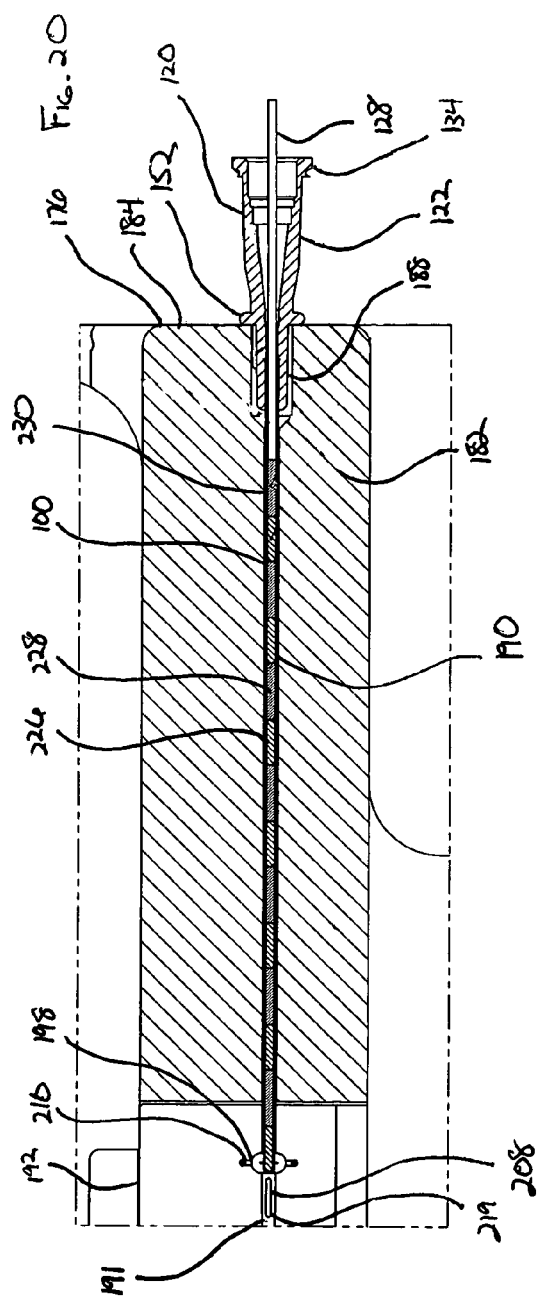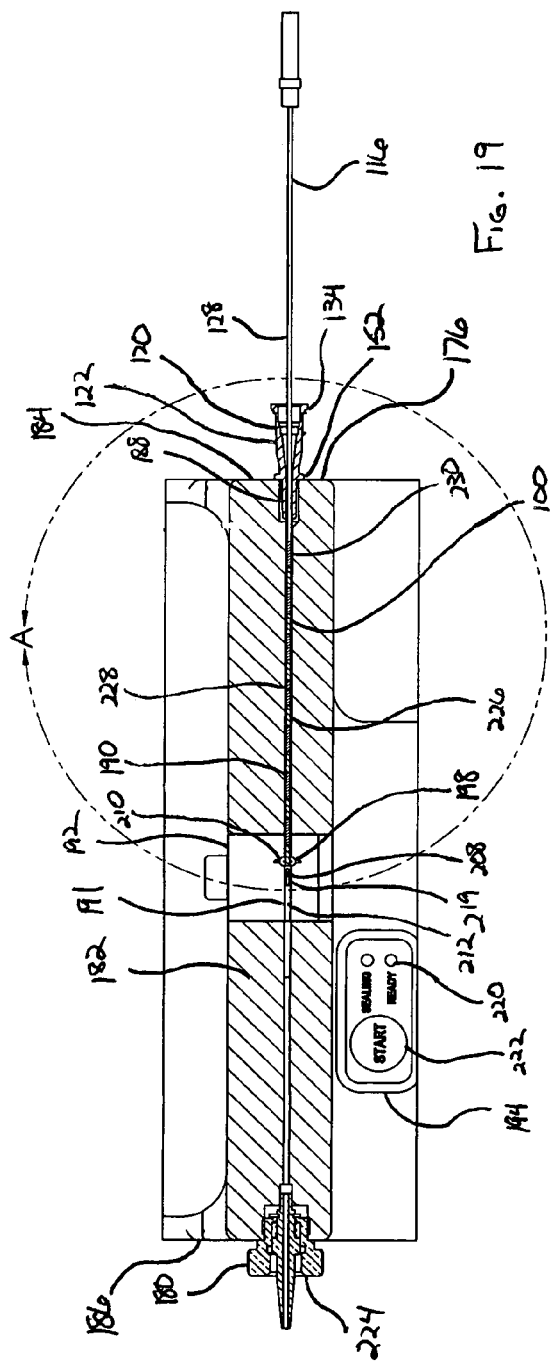

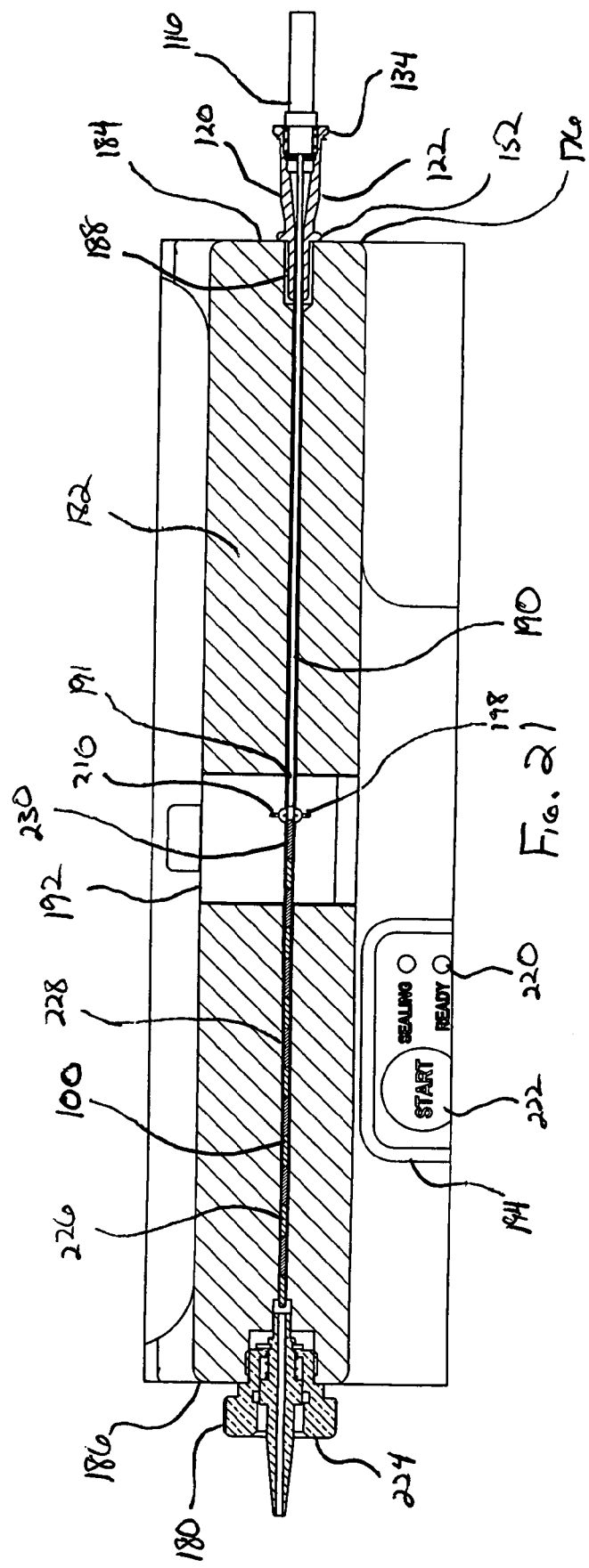

SELECTIVELY LOADABLE/SEALABLE BIORESORBABLE CARRIER ASSEMBLY FOR RADIOISOTOPE SEEDS

FIELD OF THE INVENTION

The present invention relates generally to radiation sources placed within a body for treating cancer and to holders/injectors for such radiation sources. More specifically, the present invention relates to methods and apparatus for a selectively loadable/sealable bioresorbable carrier assembly for low dose radioisotope seeds used in brachytherapy procedures.

BACKGROUND OF THE INVENTION

The use of radioisotopes for various medical procedures such as brachytherapy and the like is well known. Such uses fall into two general categories: (i) high dose radioisotopes which are temporarily positioned in relation to a patient's body for a relatively short period of time to effect the radiation treatment, and (ii) low dose radioisotopes which are permanently implanted in a patient's body with the duration of the radiation treatment determined by the strength and half-life of the radioisotope being implanted. High dose radioisotopes are typically implanted using a catheter arrangement and a device commonly known as an afterloader that advances the high dose radioisotope located on the end of a source wire through the catheter to the desired location. Low dose radioisotopes, on the other hand, are implanted using an array of implant needles with the low dose radioisotopes being encapsulated in very small containers known as seeds that are manually loaded into a series of implant needles and then ejected to form a three-dimensional grid of radioisotopes in the patient that corresponds to a dose plan as determined by the physician. The goal of the low dose brachytherapy procedure is to position this three-dimensional grid of radioisotopes seeds in and around a target cancerous tissue area.

Each of the radioisotope seeds consists of a radioactive source such as Iodine (I-125) or Palladium (Pd-103) inside a small tube-like titanium shell that is about the size of a grain of rice. These type of low dose radioactive sources emit a very low energy radiation that is primarily absorbed by the tissue immediately surrounding the radioisotope seed. This constant low energy radiation is typically emitted by the radioisotope seeds for a period of up to six months as a way to kill the cancer cells in the target area without having to subject the patient to the discomfort and risks that often accompany high dose radioisotope procedures.

One common brachytherapy procedure is the use of low dose radioisotopes to treat prostate cancer. Although brachytherapy procedures using low dose radioisotopes can be applied to many different parts of the body, it is helpful to describe a particular treatment to gain a better understanding of these treatments. Currently, the typical prostate cancer brachytherapy procedure involves positioning a predetermined number of seeds (between 1-6) within each of a series of implant needles (up to 40), the seeds being spaced apart in each needle by small spacers. Typically, a small amount of bone wax is positioned on the tip of the implant needles to prevent the seeds and spacers from falling out until they are implanted in the patient. The loaded implant needles are then positioned at the appropriate location for insertion into the perineal area of the patient using a stand that has an X-Y coordinate grid. Each needle is manually positioned in the appropriate chamber in the grid and is inserted into the patient. An ultrasound probe is used to assist the physician in guiding each of the needles to the desired location. The seeds and spacers are delivered from the tip of the implant needle using a stylet and hollow needle arrangement where the hollow needle is preferably retracted while the stylet remains in place such that the seeds are forced out of the implant needle and such that the seeds occupy the space evacuated by the needle. When the brachytherapy procedure is completed, the implanted seeds form a three-dimensional grid of radioisotope sources that implements a predetermined dose plan for treating the prostate cancer in the patient. For a more detailed background of the procedures and equipment used in this type of prostate cancer treatment, reference is made to U.S. Pat. Nos. 4,167,179 and 6,537,192.

Following the removal of the implant needles and stylet, the seeds and spacer are no longer held in position relative to one another and an opportunity exists for them to migrate within and possibly outside of the tumor. Potential migration of the radioactive seeds within the body leads to several issues. First, the time consuming step of properly positioning the needles using the ultrasound probe is defeated. Secondly, migration of seeds results in a deviation from the treatment program possibly causing some areas of cancerous tissue to be overexposed to radiation while others are underexposed. Finally, migration of the seeds outside of the tumor can lead to the seeds becoming lodged within healthy tissue or organs, for example the lungs. The healthy tissue or organ is then exposed to radiation, which will have undesired effects on healthy cells. All of these potential consequences can contribute to reducing the overall success of the brachytherapy procedure.

In order to address the issues associated with migration of the radioactive seeds, a number of methods and devices have been developed to fix the orientation of the seeds and spacers within the tumor. Laboratory analysis indicates that the use of such configurations leads to an increase in the dosimetric quantifiers for implant adequacy as compared to procedures using loose seeds and spacers. Overall, the use of such configurations tends to lead to smaller prostate glands upon completion of treatment as compared to procedures using loose seeds and spacers.

Several methods for fixing the orientation of seeds and spacers include configurations in which the seeds and spacers are interlocked to create a unitary assembly, such as described in U.S. Pat. No. 6,010,446. In other configurations, the seeds and spacers are packaged in a carrier and subsequently placed into the tumor. Typically, these carriers are preloaded and shipped from an off-site location based on a treatment plan supplied by the treating physician. U.S. Pat. Nos. 4,697,575 and 4,815,449 describe a bioresorbable elongated member that carries a fixed number of multiple radioisotopes seeds. The member is heated to secure the relative positions of the seeds and spacers and make the elongated member sufficiently rigid so as to serve as the implanting needle. U.S. Pat. No. 5,460,592 describes a pre-loaded bioresorbable strand that is pre-loaded with ten seeds spaced at equal distances for use in a conventional metal implant needle and is commercially available under the Rapid Strand™ brand name. A physician uses a cutting jig during the brachytherapy procedure to cut each strand in order to provide the desired number of seeds to be loaded into the implant needle at a given treatment location. While the Rapid Strand™ strands have proven commercially successful, there are radiation exposure risks when cutting the strand if a seed is potentially nicked during the cutting process, in addition to limitations on the options of a physician in terms of dosage planning due to the pre-loaded nature of the strands. U.S. Pat. No. 6,264,600 describes a similar arrangement that uses a hollow suture member with multiple seeds and spacers preloaded into the suture member. Instead of heating the suture member or using a jig to cut the suture member, an open front end of the suture member is made long enough to extend past the tip of an implant needle and the tip of the implant needle is used as the guide for the physician to cut the suture member to the desired length prior to implant. U.S. Pat. Nos. 6,450,937 and 6,530,875 describe needle arrangements that utilize open ended and translucent needle carrier tubes as part of the loading process to permit visual inspection of the arrangement of seeds and spacers to be loaded, however, these needle carrier tubes are not intended to be implanted as part of the brachytherapy procedure. U.S. Pat. No. 6,679,824 describes a single stranded bioresorbable material that is preloaded with seeds by placing the seeds in slits made along the material and then preferably melting the material around each seed.

While the use of such fixed orientation seed and spacer configurations has lead to improvements in brachytherapy procedures for treating prostate cancer, the current configurations suffer in several areas. First, the use of interlocking seeds and spacers does not eliminate the potential for jamming within the insertion needle as they are advanced by an insertion stylet. Secondly, preloaded carriers do not provide physicians with any flexibility to alter the treatment program based on observations during the procedure. Thirdly, the cutting of carriers or sutures carries a risk of radiation exposure in the event that a seed is nicked during the cutting process. Finally, the preloaded nature of these carriers can lead to verification issues as the radiophysicist must still verify seed potency prior to use, thus requiring the removal of at least a portion of the preloaded carrier. It would be desirable to provide a seed carrier arrangement that offered the advantages of fixed orientation seed and spacer configurations while overcoming the problems and limitations presented by existing arrangements.

SUMMARY OF THE INVENTION

The present invention provides a selectively loadable/sealable bioresorbable carrier assembly for low dose radioisotope seeds used in brachytherapy procedures. The selectively loadable/sealable bioresorbable carrier assembly comprises a bioresorbable tube having a closed distal end and a proximal open end. The bioresorbable tube is oriented with respect to a loading station such that a selectable arrangement of elements, including at least one radioactive seed, are loaded into the bioresorbable tube through the proximal open end. After the bioresorbable tube is selectably loaded, the bioresorbable tube is transferred to a finishing station that includes an automated heat source. The finishing station positions the bioresorbable tube based on the selectable arrangement of elements such that the automated heat source heat seals the bioresorbable tube at the proximal end of the selectable arrangement of elements. Once sealed, the bioresorbable tube maintains the arrangement of elements during use.

The bioresorbable carrier assembly is configured such that an arrangement of radioactive seeds and spacer members can be selectively loaded at the treatment facility just prior to the brachytherapy procedure. Most preferably, the seeds and spacers are precisely loaded by an automated loading system. By allowing a medical professional to load the bioresorbable carrier assembly at the time of use, the bioresorbable carrier assembly of the present invention provides treatment flexibility to the medical professional that is unavailable with the preloaded needles and carriers currently in use. This flexibility allows the medical professional to selectively modify the treatment program based on observations made at the time of insertion. Furthermore, the bioresorbable carrier system of the present invention eliminates the radiological testing and disposal issues present with preloaded carriers as seed potency can be determined prior to individual placement within the bioresorbable carrier thereby eliminating the need to remove and separately test individual seeds. When using an automated loading system, the risk of radiation exposure to medical personnel is reduced through the use of an automated process to test seed potency and load the bioresorbable carrier.

In a preferred embodiment, a selectable arrangement of elements including radioactive seeds and spacers are retained and positioned within a bioresorbable tube having a distal closed end, a proximal open end and lumen therebetween. The bioresorbable tube is constructed so as to allow the use of industry standard elements. Furthermore, the bioresorbable tube is constructed for use in conjunction with industry standard seeding needles. When the bioresorbable tube is heat sealed, the elements are retained in the selectable arrangement throughout the duration of a treatment program such as a brachytherapy procedure. The bioresorbable tube eliminates the potential for seed migration such that the possibility of exposing healthy tissue and/or organs to harmful radiation is eliminated.

In another embodiment, the present invention is directed to a method for loading a selectable arrangement of radioactive seeds and spacers into a bioresorbable tube for use in brachytherapy procedures.

In another embodiment, the present invention is directed to a system for loading a selectable arrangement of radioactive seeds and spacers into a bioresorbable tube for use in brachytherapy procedures.

BRIEF DESCRIPTION OF THE DRAWINGS

FIG. 1 is a side view of an embodiment of a bioresorbable carrier tube of the present invention.

FIG. 2 is a detailed view of the bioresorbable carrier tube of FIG. 1 taken at detail A of FIG. 1.

FIG. 3 is a perspective view of a packaging configuration.

FIG. 4 is a section view of the packaging configuration of FIG. 3.

FIG. 5 is an exploded, perspective view of a carrier assembly.

FIG. 6 is a section view of the carrier assembly of FIG. 5.

FIG. 7 is a perspective view of a carrier tube assembly apparatus.

FIG. 9 is a perspective view of the carrier tube assembly apparatus of FIG. 7.

FIG. 10 is a perspective view of an automated loader including the carrier tube assembly apparatus of FIG. 7.

FIG. 11 is a perspective view of a shield.

FIG. 12 is a plan view of the shield of FIG. 11.

FIG. 13 is an exploded, perspective view of a heating module.

FIG. 14 is a perspective view of the heating module of FIG. 13.

FIG. 15 is a plan view of the heating module of FIG. 13.

FIG. 16 is a section view of the heating module of FIG. 13 taken along line B-B of FIG. 15.

FIG. 17 is a side view of the heating module of FIG. 13.

FIG. 18 is a section view of the heating module of FIG. 13 taken along line C-C of FIG. 17.

FIG. 19 is a sectional, plan view of a positioning assembly including the carrier assembly of FIG. 6.

FIG. 20 is a detailed view of the positioning assembly of FIG. 19.

FIG. 21 is a sectional, plan view of the positioning assembly of FIG. 19.

DETAILED DESCRIPTION OF THE PREFERRED EMBODIMENTS

Figure 8:
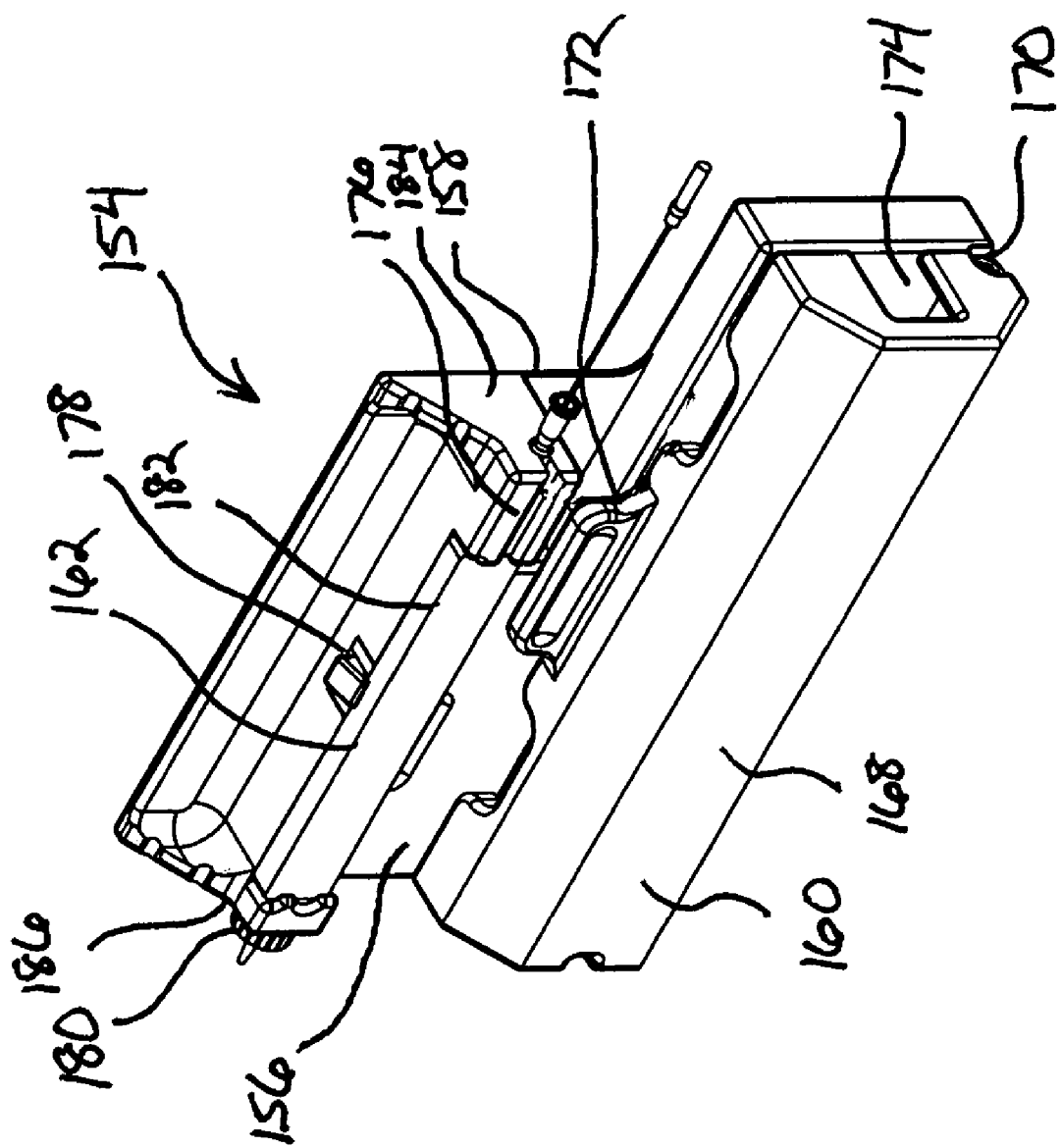
FIG. 8 is a perspective view of the carrier tube assembly apparatus of FIG. 7.

The bioresorbable carrier assembly of the present invention allows for physicians to precisely deliver a selectable arrangement of low dose radioisotope seeds and spacers into a tumor. In a preferred embodiment, a bioresorbable tube is automatically loaded and sealed using an automated loading machine. As contained herein, the bioresorbable carrier tube assembly of the present invention is described with reference to prostate brachytherapy treatment. It will be understood that the bioresorbable carrier assembly is contemplated for use in other brachytherapy procedures that benefit from the precise delivery and retainment of low dose radioisotope seeds within a tumor.

As illustrated in FIGS. 1 and 2, an embodiment of a bioresorbable tube 100 of the present invention comprises a length of bioresorbable tubing. Bioresorbable tube 100 is comprised of a suitable bioresorbable polymer or copolymer, for example polymers or copolymers of polyglycolic acid, polylactic acid, polyester amides of glycolic or lactic acids, polydioxanone and the like. It will be understood that the length of time required for bioresorbable tube 100 to break down in the body is designed to be long enough to maintain the radioactive seeds and spaced in position for the intended duration of the brachytherapy. In a preferred embodiment, bioresorbable tube 100 comprises a commercially available polymer such as polyglactin 910, polyglycaprone 25 or polydioanone. Bioresorbable tube 100 is defined by a distal closed end 102, a proximal open end 104 and a lumen 106 therebetween. Lumen 106 defines a tube inside diameter 110 while a tube wall 108 defines a tube outside diameter 112. In a preferred embodiment, tube inside diameter 110 is 0.036 inches while the tube outside diameter 112 is 0.039 inches. Bioresorbable tube 100 is constructed such that the tube inside diameter 110 allows for loading commercially available radioactive seeds and spacers such as those manufactured by Mentor Corporation of Santa Barbara, Calif., within the lumen 106. Bioresorbable tube 100 is further constructed such that the tube outside diameter 112 allows the bioresorbable tube 100 to be loaded into commercially available seeding needles. Bioresorbable tube 100 has a tube length 113. In one embodiment, tube length 113 exceeds 70 mm.

Bioresorbable tube 100 is preferably shipped as a component of a packaging kit 114 as depicted in FIGS. 3 and 4. The packaging kit 114 includes the bioresorbable tube 100, a loading stylet 116, a packaging tube 118, and a loading assembly 120. The packaging kit 114 allows a user to quickly confirm that all components have been received. Furthermore, the packaging kit 114 provides for immediate attachment to a loading means as described later without requiring any assembly or component manipulation.

Loading assembly 120, as further depicted in FIGS. 5 and 6, comprises a loading tube 122 and a loading spring 124. As illustrated in FIGS. 5, 6 and 7, the loading assembly 120 and the loading stylet 116 are arranged in a loading orientation 126 described in more detail below. Loading stylet 116 comprises a rod 128 and a handle 130. Rod 128 is preferably a solid rod dimensioned to fit within the lumen 106. Rod 128 can be constructed of metallic or polymeric materials. Rod 128 is fixedly attached to the handle 130 at a stylet flange 132. Handle 130 includes a circumferential handle flange 133. In a preferred embodiment, handle 130 comprises a polymeric material molded over the rod 128. Loading tube 122 comprises a loading connector 134. Loading tube 122 further comprises a continuous loading tube lumen 136 having a tapered lumen portion 138. Tapered lumen portion 138 includes a circumferential loading spring channel 142. The loading tube lumen 136 defines a continuous lumen between a loading end 146 and an unloading end 148. As shown in FIG. 6, the proximal open end 104 of bioresorbable tube 100 is dimensioned to reside within the tapered lumen portion 138. In addition, a circumferential application of bone wax 149 in proximity to the proximal open end 104 as illustrated in FIGS. 1 and 2 serves to prevent bioresorbable tube 100 from falling out of the tapered lumen portion 138. Loading tube 122 also includes a circumferential alignment flange 152. Loading connector 134 is dimensioned and adapted for operable connection to a fitting such as a Luer lock or other comparable fitting.

A tube assembly apparatus 154 is shown in FIGS. 7, 8 and 9. The tube assembly apparatus 154 comprises a frame member 156 having a mounting surface 158. Attached to frame member 156 is a loading station 160, a finishing station 162 and a power connector 164. In a preferred embodiment, tube assembly apparatus 154 is operably attached to an automated loader 166 as shown in FIG. 10. An example of a suitable automated loader 166 is the Iso-Loader® family of products manufactured by Mentor Corporation of Santa Barbara, Calif., and described in U.S. Pat. Nos. 6,537,192 and 6,616,593, as well as U.S. patent application Ser. Nos. 10/010,734; 10/010,968; 10/355,603; and 10/375,656, all of which are herein incorporated by reference in their entirety.

Loading station 160 comprises a hinged cover 168 attached to the frame member 156 at a hinge 170. Hinged cover 168 includes a handle 172 and defines a loading cavity 174. Loading cavity 174 is sized so as to fully accommodate the packaging kit 114. Hinged cover 168 is manufactured of a suitable radiation shielding material such as metal, lead-doped glass or suitable radiation absorbing plastic polymers.

Finishing station 162 comprises a positioning assembly 176, a heating assembly 178, a mounting assembly 180 and a shield 182 shown in FIGS. 11 and 12. Shield 182 can include a measuring scale 183 and a sealing mark 185. Finishing station 162 is generally defined by a tube insertion end 184 and a tube removal end 186. Positioning assembly 176 includes a loading tube channel 188 aligned with a finishing channel 190 to define a continuous channel 191 extending from the tube insertion end 184 to the tube removal end 186.

Heating assembly 178 comprises a heating module 192 and a control module 194. Heating module 192 as shown in FIGS. 13, 14, 15, 16, 17 and 18, comprises a heating frame 196, a heating element 198, a retaining latch 200, a latch pin 202, a pair of latch springs 204a, 204b, a pair of heater leads 206a, 206b and a positioning spring 208. Heating element 198 typically comprises a single length of nichrome wire, though other heating means exhibiting similar heating characteristics could be used. Heating frame 196 defines a heater cavity 210, a heater channel 212, a pin throughbore 214, a latch cavity 216 and a spring cavity 218. A spring opening 219 is located within heater channel 212. Control module 194 comprises a status indicator 220, such as a pair of LED's indicating a sealing status and a ready status, and a cycle initiator 222 such as a push-button or switch. Mounting assembly 180 comprises a mounting connector 224 aligned and coupled with the finishing channel 191. Mounting connector 224 can comprise a standard fastener such as a Luer lock.

In general, bioresorbable tube 100 is used to fixedly position radioactive seeds within the body during a brachytherapy procedure. Prior to placing the bioresorbable tube 100 within the body, bioresorbable tube 100 is loaded with radioactive seeds according to the desired treatment plan. In a preferred embodiment, bioresorbable tube 100 is loaded using the automated loader 166 which can incorporate a variety of testing and safety features to speed the loading of the bioresorbable tube 100. In an alternative embodiment, bioresorbable tube 100 is loaded via a manual loading process, for example hand loading with a tweezer. The bioresorbable tube 100 suitably retains and positions the radioactive seeds without regard as to the method of loading.

Use of the bioresorbable tube 100 is described with respect to an embodiment utilizing the automated loader 166. As shown in FIG. 10, the automated loader 166 is configured for operably mounting the tube assembly apparatus 154. In a preferred embodiment, the automated loader 166 is adapted to include a power supply for interfacing with the power connector 164 during coupling of the tube assembly apparatus 154 to the automated loader 166. Alternatively, the power connector 164 can be connected to a stand-alone cord and plug. As depicted in FIG. 6, the hinged cover 160 is rotatably opened such that the packaging kit 114 can be coupled to the automated loader 166. By shipping and attaching the packaging kit 114, a user can be assured that all of the necessary components are present and no assembly or disassembly is required prior to attachment to the automated loader 166. In the packaging kit 114, the bioresorbable tube 100 is positioned within the loading tube lumen 136. Once the packaging kit 114 is fixedly coupled to the automated loader 166, for example using a Luer lock connection for interconnecting to the loading connector 134, the hinged cover 168 is preferably rotated to a closed position such that the bioresorbable tube 100 within the packaging kit 114 is fully positioned within the loading cavity 174. The hinged cover 168 shields nearby personnel from potential radiation exposure during loading of the bioresorbable tube 100.

Automated loader 166 includes insertion means for slidably inserting a selectable arrangement of elements comprising low dose radioactive seeds 226 and spacers 228 within the bioresorbable tube 100. Generally, automated loader 166 loads a minimum of at least one radioactive seed 226. Radioactive seeds 226 and spacers 228 can comprise any commercially available configuration having dimensions slightly less than the carrier tube inside diameter 110. Examples of suitable radioactive seeds 226 include Iodine (I-125) and Palladium (Pd-103) seeds manufactured by Mentor Corporation of Santa Barbara, Calif., with a seed length of approximately 4.5 mm and a seed diameter of approximately 0.8 mm. Examples of suitable spacers 228 include Accu-Space™ and BioSpacer 910™ spacers available from CP Medical of Portland, Oreg. Spacer 228 can be provided in various lengths, for example 5.5 mm or 10 mm, such that the positioning of radioactive seeds 226 can be conformed to the treatment plan. Automated loader 166 proceeds to load the bioresorbable tube 100 with the radioactive seeds 226 and spacers 228 as dictated by the treatment plan and as disclosed in the aforementioned and incorporated IsoLoader™ patents and published patent applications. The bioresorbable tube 100 can be loaded with any variety of radioactive seeds 226 and spacers 228 with the only limitation being that the loading arrangement not exceed 70 mm in length. During loading, the radioactive seeds 226 and spacers 228 are advanced into the bioresorbable tube 100 through the proximal open end 104 whereby they are advanced through the lumen 106 and whereby further advancement is prevented by distal closed end 102.

Following the loading of the bioresorbable tube 100 with radioactive seeds 226 and spacers 228, the hinged cover 168 is rotatably opened as depicted in FIG. 10 such that the loading tube 122 can be removed from the automated loader 166. At this point, loading stylet 116 and packaging tube 118 are removed such that loading assembly 120 can be positioned with respect to the positioning assembly 176, as shown in FIGS. 8, 19, 20 and 21. Packaging tube 118 can be discarded while loading stylet 116 is set aside for use as described below.

As illustrated in FIGS. 8, 19, 20 and 21, in positioning the loading assembly 120 with respect to the positioning assembly 176, the loading tube 122 is placed within the loading tube channel 188 and slidingly advanced until the circumferential alignment flange 152 is in contact with the tube insertion end 184. At this point, a portion of the loading tube lumen 136 including the bioresorbable tube 100 resides within the finishing channel 190. When the bioresorbable tube 100 is located within the finishing channel 190, the shield 182 prevents radiation exposure to a user during the finishing process.

Once the loading assembly 120 is fully positioned with respect to the positioning assembly 176, a user directs the rod 128 of loading stylet 116 into the tapered lumen portion 138 as depicted in FIG. 21. The rod 128 is slidingly advanced through the tapered lumen portion 138 such that the rod 128 enters into the lumen 106 whereby the rod 128 comes into contact with a proximalmost element 230, i.e., a radioactive seed 226 or spacer 228. As the rod 128 is further advanced, the bioresorbable tube 100 is advanced out of the loading tube lumen 136 and into the finishing channel 190 due to the rod 128 pushing the combination of radioactive seeds 226 and spacers 228 against the distal closed end 102. The advancement of the rod 128 overcomes the retaining features, i.e., the proximal open end 104 and the bone wax 149, that previously acted to retain the bioresorbable tube 100 within the loading tube 122. As rod 128 is advanced, the stylet flange 132 comes into contact with the loading spring 124 whereby further advancement of the rod 128 causes compression of the loading spring 124. Rod 128 is fully advanced until the circumferential handle flange 133 abuts the loading end 146. At this point, the user releases the handle 130 whereby the loading spring 124 relaxes such that the rod 128 is directed away from the rearmost element 230. In a preferred embodiment, loading spring 124 relaxes a distance of approximately 2 mm so as to create an approximately 2 mm gap between the rod 128 and the proximalmost element 230. Loading stylet 116, loading tube channel 188 and finishing channel 190 are precisely dimensioned such that when loading spring 124 relaxes, the heating element 198 is aligned within the approximately 2 mm gap between the rod 128 and the proximalmost element 230. The heating element 198 is properly positioned within the 2 mm gap without regard to the number or configuration of radioactive seeds 226 and spacers 228 loaded within the bioresorbable stand 100 as dictated by the treatment plan. While a 2 mm gap is described, it will be understood that any gap sufficient to permit the seeding to occur could be used. In another embodiment, the heating element 198 could be aligned with a special rearmost element 230 that is designed to melt as part of the heat sealing process.

Once the bioresorbable tube 100 is properly positioned with respect to the heating element 198, the user seals the lumen 106 at the 2 mm gap. The user presses or switches the cycle indicator 222 to initiate the sealing process. The cycle initiator 222 communicates with an internal microprocessor or electronic circuit integral to the heating assembly 178 such that the heater leads 206*a*, 206*b* are powered. The heater leads 206*a*, 206*b* cause the heating element 198 to quickly heat whereby the bioresorbable tube 100 melts within the 2 mm gap. During the heating process, the status indicator 220 provides a visual feedback, i.e., a light, indicating the heating condition. The heater leads 206*a*, 206*b* are typically powered from two to fifteen seconds to accommodate polymeric variations within bioresorbable carrier tubes 100 of differing manufacturing batches. Once the heating time is completed, the heater leads 206*a*, 206*b* are deenergized such that a newly formed, proximal sealed end 232 is allowed to cool. After cooling for approximately 3 seconds, the microprocessor or electronic circuit directs the status indicator 220 to indicate that a sealed tube 234 is complete.

Figure 22:
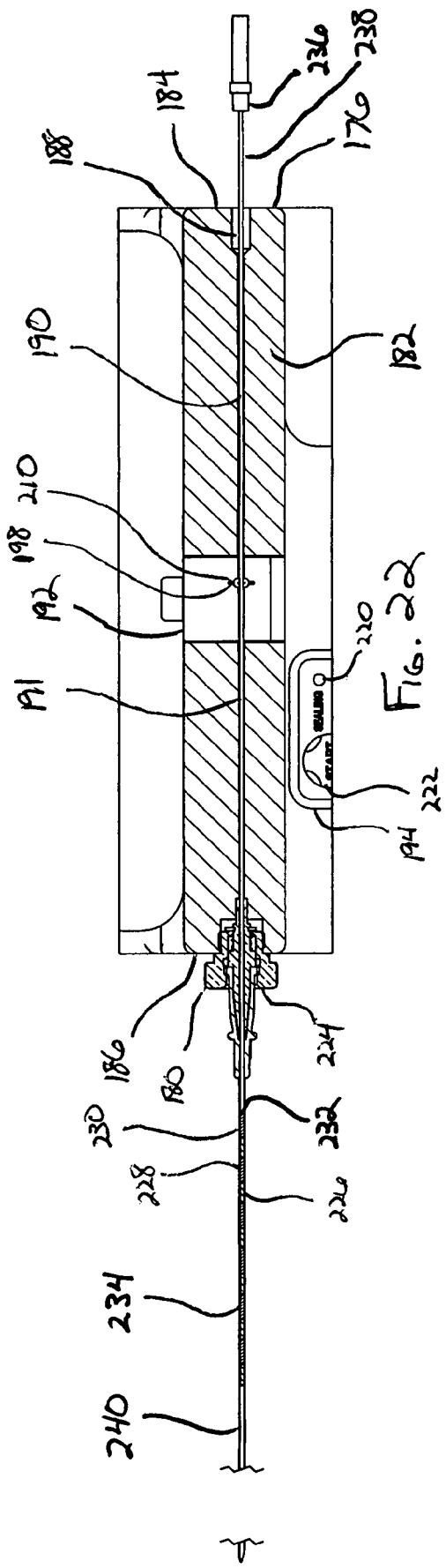
FIG. 22 is a sectional, plan view of the positioning assembly of FIG. 19.

Following the assembly of sealed carrier tube 234, a user positions a second stylet 236 as shown in FIGS. 9 and 22 in a similar manner as previously described with respect to the loading stylet 116. Second stylet 236 has a second stylet rod 238 with a length greater than the continuous channel 191. At any time, either prior to, during assembly or after assembly of the sealed tube 234, the user can attach a seeding needle 240 or alternative delivery vehicle to the mounting connector 224. The user advances the second stylet rod 238 through the continuous channel 191 whereby the second stylet rod 238 contacts the proximal sealed end 232 causing the sealed tube 234 to be advanced into the seeding needle 240. At this point, the seeding needle 240 is detached and ready for use in placing the sealed tube 234 within cancerous tissue.

Although various embodiments of the present invention have been disclosed here for purposes of illustration, it should be understood that a variety of changes, modifications and substitutions may be incorporated without departing from either the spirit or scope of the present invention.

What is claimed:

1. A system for selectively loading and sealing a plurality of bioresorbable carriers for low dose radioisotope seeds comprising:
    a plurality of bioresorbable tubes each having a distal closed end and a proximal open end and a lumen therebetween;
    a loading station that permits a user to load a selectable arrangement of elements including at least one radioisotope seed into the lumen though the proximal open end of each bioresorbable tube; and
    a finishing station including an automated heat source that selectively seals the proximal open end of each bioresorbable tube at a sealing position along the bioresorbable tube that is generally adjacent to a proximal end of the selectable arrangement of elements such that the selectable arrangement of elements is retained within the bioresorbable tube;
    such that the sealing position for different ones of the plurality of bioresorbable tubes is located at different distances from the distal closed end dependent upon the selectable arrangement of elements advanced into that bioresorbable tube.

2. The system of claim 1, wherein the loading station is an automated loading station.

3. The system of claim 2, further comprising a loading tube external and coaxial to each bioresorbable tube and having two open ends with a loading adapter at one end that interfaces with an aperture on the automated loading station.

4. The system of claim 3, wherein the loading adapter comprises a flared portion of the loading tube with locking structure thereon that mates with corresponding structure proximate the aperture on the automated loading station.

5. The system of claim 3, wherein at least a portion of the loading tube is transparent to permit visual inspection of the selectable arrangement of elements.

6. The system of claim 3, further comprising a packaging tube external and coaxial to at least a portion of each loading tube and a removable stylet disposed between the packaging tube and the loading tube at the end opposite to the loading adapter.

7. The system of claim 3, wherein at least a portion of the loading tube and a corresponding portion of the packaging tube are transparent to permit visual inspection of the selectable arrangement of elements.

8. The system of claim 2, wherein the plurality of bioresorbable tubes are selectively loaded in accordance with a desired treatment plan.

9. The system of claim 1, further comprising:
    a loading tube external and coaxial to each bioresorbable tube and having an open end corresponding to the proximal end of the bioresorbable tube and an open distal end corresponding to the distal closed end of the bioresorbable tube; and
    means for releasably retaining the bioresorbable tube within the loading tube.

10. The system of claim 9, wherein the means for releasably retaining the bioresorbable tube comprises a friction fit created by a material surrounding at least a portion of the bioresorbable tube proximate the proximal end of the bioresorbable tube that interfaces with a portion of an interior surface of the proximal end of the loading tube.

11. The system of claim 9, wherein the finishing station comprises:
    a positioning channel having a first end and a second end, the first end adapted to receive the bioresorbable tube from the distal end of the loading tube when a stylet is advanced into the proximal open end of the bioresorbable tube;
    a resilient member at the second end of the positioning channel that compresses when the stylet advances the bioresorbable tube into the resilient member and recoils to position the bioresorbable tube at a sealing position; and
    a heating element positioned along the positioning channel proximate the sealing position that is selectively activated to heat seal the bioresorbable tube;
    such that each bioresorbable tube is positioned at the sealing position in response to a combined length of the selectable arrangement of elements loaded into that bioresorbable tube.

12. A method for retaining a selectable arrangement of elements within a brachytherapy carrier comprising:
    loading a bioresorbable tube with the selectable arrangement of elements wherein the selectable arrangement of elements include at least one low dose radioisotope seed, the selectable arrangement of elements being directed into the bioresorbable tube at a proximal open end and retained by a distal closed end;

defining a sealing position along the length of the bioresorbable tube, the sealing position being determined by the selectable arrangement of elements within the bioresorbable tube, the sealing position being generally adjacent a proximalmost element and wherein the sealing position is in proximity to an automated heat source;

sealing the bioresorbable tube with the automated heat source, the automated heat source melting the bioresorbable tube at the sealing position such that the selectable arrangement of elements are encased within a sealed bioresorbable tube.

13. The method of claim 12, wherein the selectable arrangement of elements includes at least one spacer.

14. The method of claim 12, wherein the selectable arrangement of elements defines an arrangement length within a range of 4.5 mm-70 mm.

15. The method of claim 12, wherein an automated loader loads the selectable arrangement of elements into the bioresorbable tube.

16. The method of claim 12, further comprising inserting the sealed bioresorbable tube into a seeding needle such that the sealed bioresorbable tube is deliverable into a cancerous tissue.

17. The method of claim 12, wherein defining the sealing position includes placing the bioresorbable tube within a channel on a finishing station such that a stylet pushes against the proximalmost element and positions the proximalmost element adjacent the automated heat source irrespective of the selectable arrangement of elements.

18. The method of claim 12, wherein the automated heat source includes a control circuit that initiates a temperature cycle during which the bioresorbable tube is first melted followed by a cooling cycle during which the sealed bioresorbable tube is allowed to cool.

19. The method of claim 18, wherein the control circuit includes a visual indicator wherein completion of the temperature cycle is displayed.

20. The method of claim 12, wherein at least a portion of the bioresorbable tube is transparent to permit visual confirmation of the selectable arrangement of elements.

21. The method of claim 12, further comprising repeating the aforementioned steps for a plurality of bioresorbable tubes such that a plurality of sealed bioresorbable tubes are prepared as defined by a treatment plan.

22. The method of claim 21, wherein the plurality of sealed bioresorbable tubes are prepared at a treatment site.

* * * * *